(12) United States Patent
Meyer, Jr. et al.

(10) Patent No.: US 6,485,906 B2
(45) Date of Patent: *Nov. 26, 2002

(54) OLIGONUCLEOTIDES CONTAINING PYRAZOLO[3,4-D]PYRIMIDINES FOR HYBRIDIZATION AND MISMATCH DISCRIMINATION

(75) Inventors: Rich B. Meyer, Jr., Bothell, WA (US); Irina A. Afonina, Mill Creek, WA (US); Igor V. Kutyavin, Bothell, WA (US)

(73) Assignee: Epoch Pharmaceuticals, Inc., Bothell, WA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/431,385

(22) Filed: Nov. 1, 1999

(65) Prior Publication Data

US 2002/0146690 A1 Oct. 10, 2002

Related U.S. Application Data

(63) Continuation of application No. 09/054,830, filed on Apr. 3, 1998, now Pat. No. 6,127,121.

(51) Int. Cl.[7] .............................. C12Q 1/68; G01N 1/00; G01N 15/00; C07H 21/00

(52) U.S. Cl. ............................ 435/6; 422/50; 422/68.1; 536/23.1; 536/24.3; 536/24.31; 536/24.32

(58) Field of Search .................................. 435/6, 78, 77, 435/88, 24.31, 24.32; 536/23.1, 24.3, 24.33, 25.3, 25.32; 422/50, 68.1

(56) References Cited

U.S. PATENT DOCUMENTS

| 4,358,535 A | 11/1982 | Falkow et al. | 435/5 |
| 4,683,195 A | 7/1987 | Mullis et al. | 435/6 |

(List continued on next page.)

FOREIGN PATENT DOCUMENTS

| EP | 070685 | 1/1983 |
| EP | 0 320308 B1 | 6/1989 |
| EP | 0 336731 B1 | 10/1989 |
| WO | WO 90/03370 | 4/1990 |
| WO | WO 90/14353 | 11/1990 |
| WO | WO 92/10588 | 6/1992 |
| WO | WO 96/17957 | 6/1996 |
| WO | WO 96/32496 | 10/1996 |

OTHER PUBLICATIONS

Matthews et al., Analytical Biochemistry, vol. 169, pp. 1–25, 1988.

(List continued on next page.)

*Primary Examiner*—Ardin H. Marschel
(74) *Attorney, Agent, or Firm*—Townsend and Townsend and Crew, LLP

(57) ABSTRACT

Oligonucleotides in which one or more purine residues are substituted by pyrazolo[3,4-d]pyrimidines exhibit improved hybridization properties. Oligonucleotides containing pyrazolo[3,4-d]pyrimidine base analogues have higher melting temperatures than unsubstituted oligonucleotides of identical sequence. Thus, in assays involving hybridization of an oligonucleotide probe to a target polynucleotide sequence, higher signals are obtained. In addition, mismatch discrimination is enhanced when pyrazolo[3,4-d] pyrimidine-containing oligonucleotides are used as hybridization probes, making them useful as probes and primers for hybridization, amplification and sequencing procedures, particularly those in which single- or multiple-nucleotide mismatch discrimination is required.

13 Claims, 4 Drawing Sheets

U.S. PATENT DOCUMENTS

| | | | |
|---|---|---|---|
| 4,683,202 A | 7/1987 | Mullis | 435/91 |
| 4,800,159 A | 1/1989 | Mullis et al. | 435/172 |
| 4,868,105 A | 9/1989 | Urdea et al. | 435/6 |
| 4,883,750 A | 11/1989 | Whiteley et al. | 435/6 |
| 5,124,246 A | 6/1992 | Urdea et al. | 435/6 |
| 5,210,015 A | 5/1993 | Gelfand et al. | 435/6 |
| 5,419,966 A | 5/1995 | Reed et al. | 428/406 |
| 5,432,272 A | 7/1995 | Benner | 536/25 |
| 5,449,767 A | 9/1995 | Ward et al. | 536/24 |
| 5,492,806 A | 2/1996 | Drmanac et al. | 435/5 |
| 5,512,667 A | 4/1996 | Reed et al. | 536/24 |
| 5,516,641 A * | 5/1996 | Ullman et al. | 435/6 |
| 5,525,464 A | 6/1996 | Drmanac et al. | 435/6 |
| 5,556,752 A | 9/1996 | Lockhart et al. | 435/6 |
| 5,652,099 A * | 7/1997 | Conrad | 435/6 |
| 5,698,394 A * | 12/1997 | Duhamel et al. | 435/6 |
| 5,800,992 A | 9/1998 | Fodor et al. | 435/6 |
| 5,801,155 A * | 9/1998 | Kutyavin et al. | 514/44 |
| 5,824,796 A | 10/1998 | Petrie et al. | 536/26 |

OTHER PUBLICATIONS

Belousov et al., "Tripex targeting of a native gene in permeabilized intact cells: covalent modification of the chemokine receptor CCR5," Nucleic Acids Res., vol. 26(5):1324–1328 (1998).

Cardullo et al., "Detection of nucleic acid hybridization by nonradiative fluorescence resonance energy transfer," Proc. Natl. Acad. Sci. USA, vol. 85:8790–8794 (1988).

Chen et al., "Synthesis of oligodeoxyribonucleotide N3'.fwdarw.P5' phosphoramidates," Nucleic Acids Res., vol. 23(14):2661–2668 (1995).

Draper et al., "A Method for Linking Fluorescent Labels to Polynucleotides: Application to Studies of Ribosome–Ribonucleic Acid Interactions," Biochemistry, vol. 19:1774–1781 (1980).

Heid et al., "Real Time Quantitative PCR," Genome Res., vol. 6:986–994 (1996).

Livak et al., "Oligonucleatides with Fluorescent Dyes at Opposite Ends Provide a Quenched Probe System Useful for Detecting PCR Product and Nucleic Acid Hybridization," PCR Meth. App., vol. 4:357–362 (1995).

Lukhtanov et al., "Oligodeoxyribonucleotides with Conjugated Dihydropyrroloindole Oligopeptides: Preparation and Hybridization Properties," Bioconj. Chem., vol. 6:418–426 (1995).

Parris et al., "A signature element distinguishes sibling and independent mutations in a shuttle vector plasmid," Gene, vol. 117:1–5 (1992).

Sanger et al., "DNA sequencing with chain–terminating inhibitors," Proc. Natl. Acad. Sci. USA, vol. 74:5463–5467 (1977).

Seela et al., "168. Synthesis of 2'–Deoxyribofuranosides of 8–Aza–7–deazaguanine and Related Pyrazolo[3,4–d]pyrimidines," Helvetica Chimica Acta, vol. 69:1602–1613 (1986a).

Seela et al., "2'D–Desoxyribofuranoside des 6–Oxoallopurinols und verwandter 4,6–substituierter Pyrazolo[3,4–d]pyrimidine," Liebigs Ann. Chem., 1213–1221 (1986b).

Seela et al., "131.8–Aza–7–deaza–2'–deoxyguanosine: Phosphoramidite Synthesis and Properties of Octanucleotides," Helvetica Chimica Acta, 71:1191–1199 (1988a).

Seela et al., "193.8–Aza–7–deazaadenine N.sup8 –and N.sup.9 –(beta.–D–2'–Deoxyribofuranosides): Building Blocks for Automated DNA Synthesis and Properties of Oligodeoxyribonucleotides," Helvetica Chimica Acta, 71:1813–1823, (1988b).

Seela et al., "Alternating d(G–C).sub.3 and d(C–G).sub.3 hexanucleotides containing 7–deaza–2'–deoxyguanosine or 8–aza–7–deaza–2'–deoxyguanosine in place of dG," Nucleic Acids Res., vol. 17(3):901–910 (1989).

van Ness et al., "The use of oligodeoxynucleotide probes in chaotrope–based hybridization solutions," Nucleic Acids Res., vol. 19(19):5143–5151 (1991).

Wittwer et al., "Continuous Fluorescence Monitoring of Rapid Cycle DNA Amplification," Biotechniques, vol. 22(1):130–138 (1997a).

Wittwer et ;al., "The Light Cycler.TM.: A Microvolume Multisample Fluorimeter with Rapid Temperature Control," Biotechniques, vol. 22(1):176–181 (1997b).

\* cited by examiner

```
4741 AAAACTCTCA AGGATCTTAC CGCTGTTGAG ATCCAGTTCG ATGTAACCCA CTCGTGCACC
                                                              PRIMER 1
4801 CAACTGATCT TCAGCATCTT TTACTTTCAC CAGCGTTTCT GGGTGAGCAA AAACAGGAAG

4861 GCAAAATGCC GCAAAAAAGG GAATAAGGGC GACACGGAAA TGTTGAATAC TCATACTCTT
                          SUPF NUCLEOTIDE 1                11
4921 CCTTTTTCAA TATTATTGAA GCATTTATCA GG          GAATTCGAGA GCCCTGCTCG
                            18-MER
                        15-MER
              21      12-MER
         AGCTGTGGTG GGGTTCCCGA GCGGCCAAAG GGAGCAGACT CTAAATCTGC CGTCATCGAC

32    A
              36       T
              36       G
              36       A
              37       T
              37     A
              39        C
              41           A
              41           C
              43             A
              43             T
              44               T

81
        TTCGAAGGTT CGAATCCTTC CCCCACCACC ACGGCCGAAA TTCGGTACCC GGATCCTTAG

141
        CGAAAGCTAA GATTTTTTTT ACGCGTGAGC TCGACTGACT CCNNNNNNNN GAGCTCAATT

201                                                        PRIMER 2
        CGGTCGAGGT CGGGCCGCGT TGCTGGCGTT TTTCCATAGG CTCCGCCCCC CTGACGAGCA

261
        TCACAAAAAT CGACGCTCAA GTCAGAGGTG GCGAAACC
```

*FIG._1*

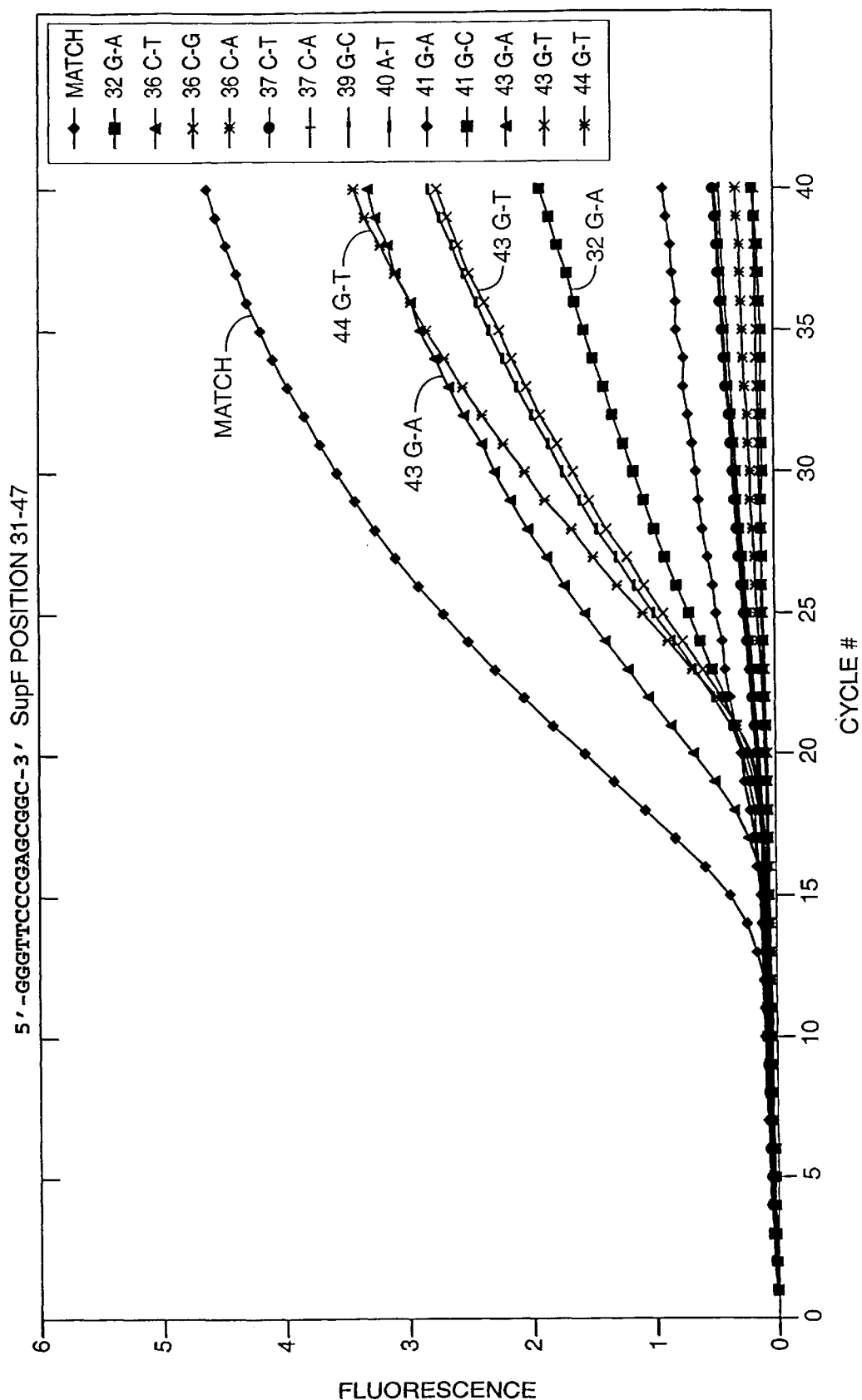
FIG._2

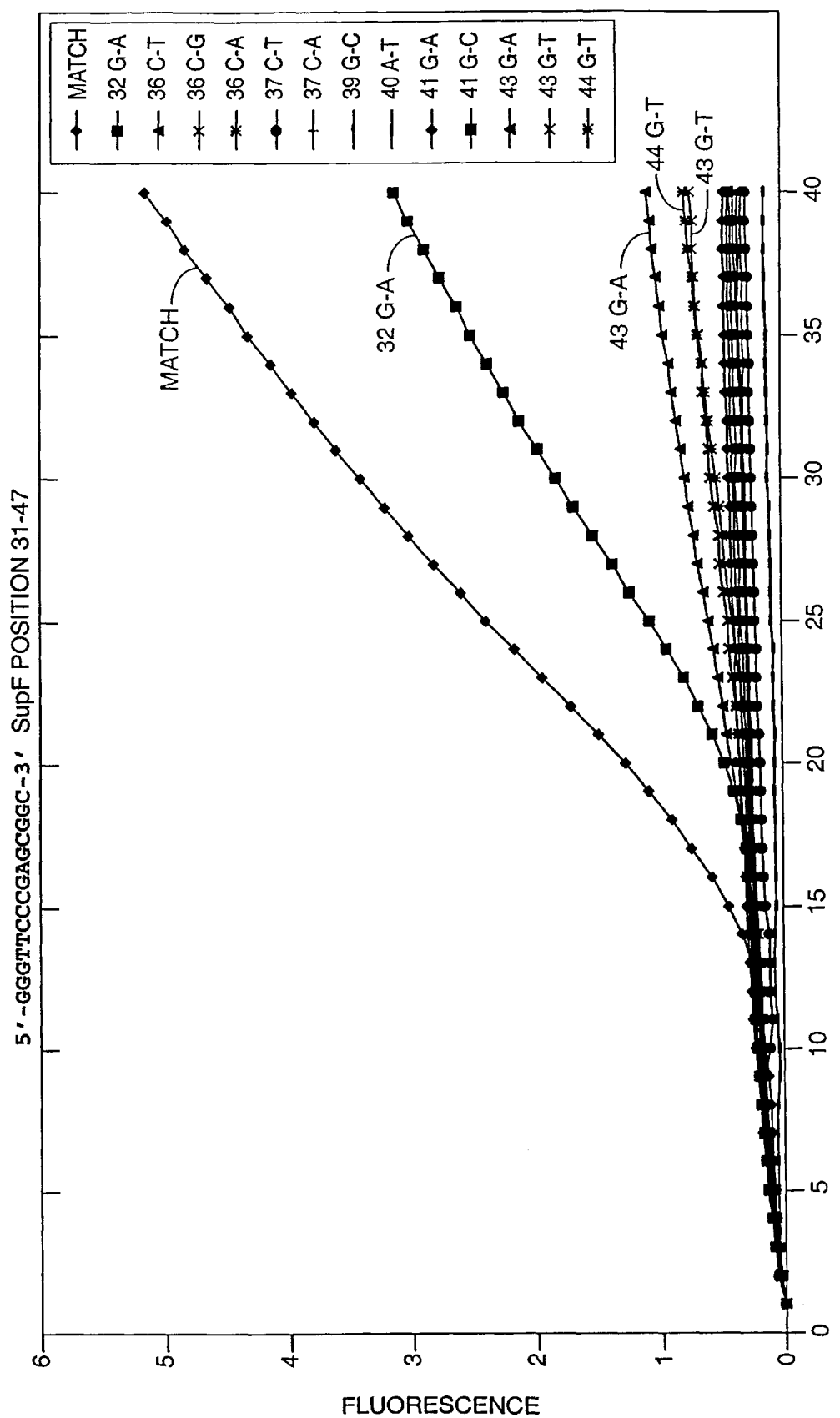
FIG._3

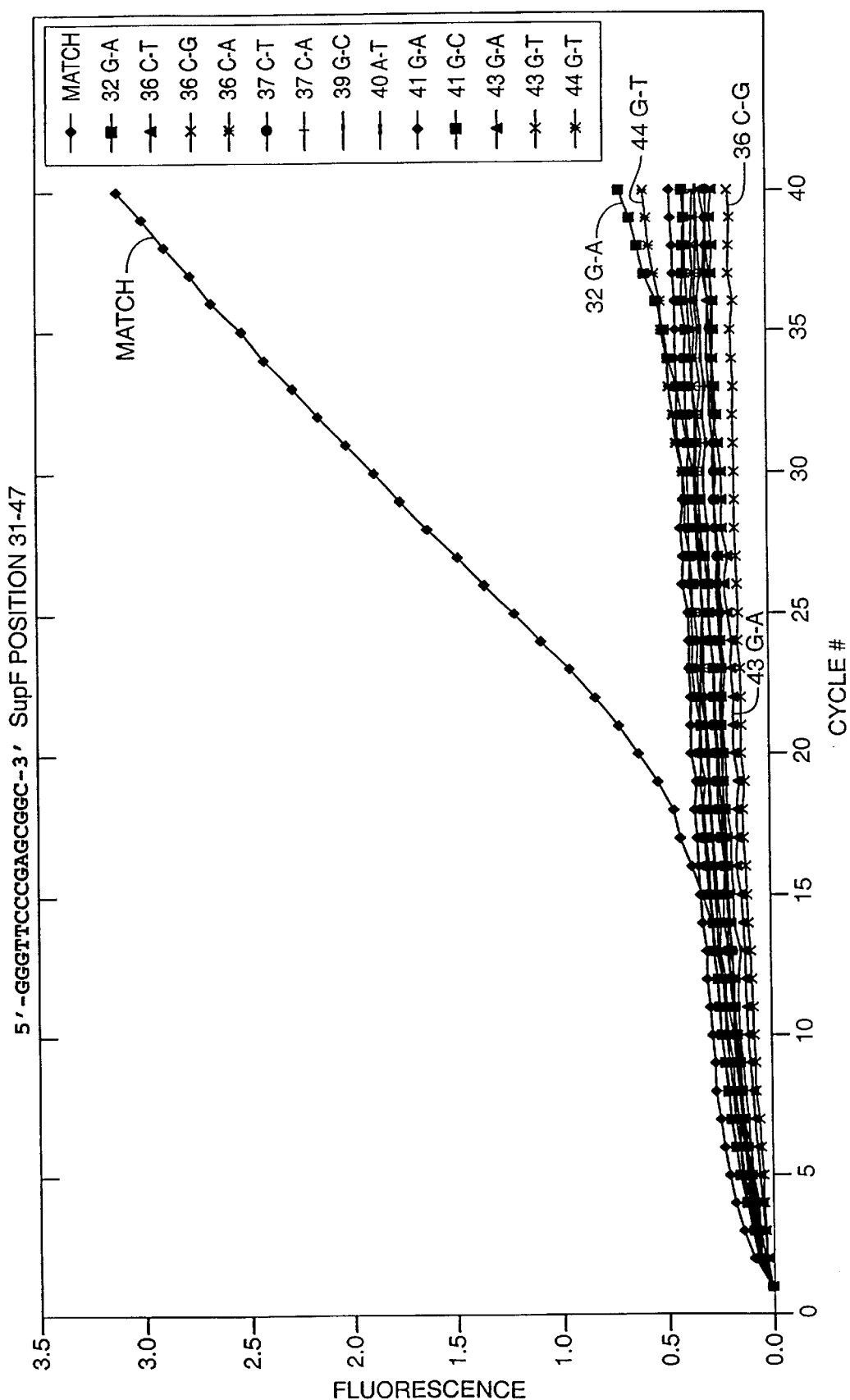
FIG._4

US 6,485,906 B2

OLIGONUCLEOTIDES CONTAINING PYRAZOLO[3,4-D]PYRIMIDINES FOR HYBRIDIZATION AND MISMATCH DISCRIMINATION

This application is a continuation of application Ser. No. 09/054,830 filed on Apr. 3, 1998, now U.S. Pat. No. 6,127,121.

TECHNICAL FIELD

This application is in the field of molecular biology relating to the use of oligonucleotides as probes and primers. It relates further to the use of modified nucleic acid bases to improve the hybridization properties and discriminatory abilities of oligonucleotides that are used as probes and primers.

BACKGROUND

Many techniques currently in use in molecular biology utilize oligonucleotides as probes and/or primers. It is often advantageous, in the practice of these techniques, to be able to distinguish between two or more sequences which are related but which differ by one or more nucleotides. For example, many mutations of clinical significance differ by only a single nucleotide from the wild-type sequence. Polymorphisms in mammalian genomes are also often characterized by sequence differences of one or a few nucleotides. The ability to make such a distinction is known as mismatch discrimination. In practical terms, mismatch discrimination describes the property by which a defined sequence oligonucleotide, at a given stringency, hybridizes strongly (one manifestation of which is that the hybrids have a high melting temperature) to a target sequence with which it is complementary along its entire length (a perfect hybrid or perfect match), but hybridizes detectably more weakly to a target sequence that is non-complementary to the sequence of the oligonucleotide at one or a few nucleotides (a mismatch). The differences in hybridization strength are such that a particular stringency can be selected at which a perfect match is detectable as a hybrid and a mismatch fails to form a hybrid.

In a nucleic acid duplex, each base pair contributes to stability. Hence, the shorter the duplex, the greater the relative contribution of each individual base pair to the stability of the duplex. As a result, the difference in stability between a perfect match and a mismatch will be greater for shorter oligonucleotides. However, short oligonucleotides hybridize weakly, even to a perfectly complementary sequence, and thus must be hybridized under conditions of reduced stringency. Thus, the potential discriminatory power of short oligonucleotides cannot be easily realized except under conditions of low stringency, which counteract their discriminatory ability. It would constitute a substantial advance in the art if it were possible to achieve mismatch discrimination, particularly for single-nucleotide mismatches, under conditions of high stringency; for example, at the elevated temperatures characteristic of most amplification reactions.

Stabilization of duplexes by pyrazolopyrimidine base analogues has been reported. Seela et al. (1988) Helv. Chim. Acta. 71:1191–1198; Seela et al. (1988) Helv. Chim. Acta. 71:1813–1823; and Seela et al. (1989) Nucleic Acids Res. 17:901–910. Pyrazolo[3,4-d]pyrimidine residues in oligonucleotides are also useful as sites for attachment of various pendant groups to oligonucleotides. See co-owned PCT Publication WO 90/14353, Nov. 29, 1990. In addition, oligonucleotides in which one or more purine residues have been substituted by pyrazolo[3,4-d]pyrimidines display enhanced triplex-forming ability, as disclosed, for example, in Belousov et al. (1998) Nucleic Acids Res. 26:1324–1328. Pyrazolopyrimidines, when incorporated into an oligonucleotide, may provide improved duplex and triplex formation. U.S. Pat. No. 5,594,121.

DISCLOSURE OF THE INVENTION

It is an object of the present invention to provide new oligonucleotide compositions with improved properties related to hybridization and mismatch discrimination. It is a further object of the present invention to provide improved methods for hybridization, primer extension, hydrolyzable probe assays, PCR, single-nucleotide mismatch discrimination, nucleotide sequence analysis, array analysis and related techniques involving the use of oligonucleotides as probes and/or primers.

Accordingly, in one aspect, the present invention provides modified oligonucleotide compositions comprising one or more pyrazolo[3,4-d]pyrimidine base analogues substituted for at least one purine. In preferred embodiments, the guanine analogue 6-amino-1H-pyrazolo[3,4-d]pyrimidin-4 (5H)-one (ppG) is substituted for guanine, and/or the adenine analogue 4-amino-1H-pyrazolo[3,4-d]pyrimidine (ppA) is substituted for adenine. In other embodiments, the guanine analogue 1H-pyrazolo[3,4-d]pyrimidin-4(5H) one (ppI) is substituted for guanine. The pyrazolo[3,4-d] pyrimidine-substituted oligonucleotides can comprise, in addition, other moieties such as detectable labels and/or minor groove binders and/or other types of modified bases or base analogues.

Another aspect of the invention is a method for hybridization of nucleic acids, wherein at least one of the nucleic acids is a modified nucleic acid wherein one or more purine residues are substituted with a pyrazolo[3,4-d]pyrimidine base analogue. This method provides higher melting temperatures and enhanced mismatch detection. The improved hybridization methods provided by the present invention can be used in techniques which include, but are not limited to, hybridization, primer extension, single-nucleotide polymorphism detection, hydrolyzable probe assays, cDNA synthesis, nucleotide sequence determination, amplification reactions, and other techniques such as are known to those of skill in the art.

When the guanine bases in an oligonucleotide are replaced by the guanine analogue ppG, the $T_m$ values of probes containing the analogues are slightly higher than those of oligonucleotide probes containing guanine. Hence, G-containing and ppG-containing oligonucleotides perform similarly in hybridization assays. However, when ppG-substituted oligonucleotides are used as hydrolyzable probes (described infra and see U.S. Pat. No. 5,210,015), two properties are significantly enhanced. First, ppG-substituted probes are more effective at mismatch discrimination, as measured by higher signal-to-noise values comparing the fluorescent signal obtained from a perfectly-matched hybrid with that from a hybrid containing a single-nucleotide mismatch. In addition, ppG-substituted probes provide higher absolute signal from a perfectly-matched target.

BRIEF DESCRIPTION OF THE DRAWINGS

FIG. 1 shows the nucleotide sequence of the E. coli supF gene contained in the plasmid pSP 189 (SEQ ID NO.: 1). Locations of the target sequences for amplification primers are shown as "Primer 1" and "Primer 2." Also shown are the target sequences for the probes (designated "12-mer," "15-mer" and "18-mer"), and the single-nucleotide substitutions that were introduced into the probe target sequences (shown underneath the probe target sequences).

FIG. 2 shows results of a hydrolyzable probe assay, using minor groove binder (MGB)-conjugated 15-mers (SEQ ID NO.: 5) as probes. The target was the *E. coli* supF gene. Annealing/elongation was conducted at 72° C. for 20 sec per cycle.

FIG. 3 shows results of a hydrolyzable probe assay, using MGB-conjugated 15-mers (SEQ ID NO.: 5) as probes. In this experiment, all guanine bases in the probes were substituted with the guanine analogue ppG. All probes also contained a conjugated MGB. The target was the *E coli* supF gene. Annealing/elongation was conducted at 72° C. for 20 sec per cycle.

FIG. 4 shows results of a hydrolyzable probe assay, using MGB-conjugated 15-mer probes (SEQ ID NO.: 5) in which all guanine bases in the probe were substituted with the guanine analogue ppG. The target was the *E. coli* supF gene. Annealing/elongation was conducted at 75° C. for 20 sec per cycle.

MODES FOR CARRYING OUT THE INVENTION

The practice of the present invention will employ, unless otherwise indicated, conventional techniques in organic chemistry, biochemistry, oligonucleotide synthesis and modification, bioconjugate chemistry, nucleic acid hybridization, molecular biology, microbiology, genetics, recombinant DNA, and related fields as are within the skill of the art. These techniques are fully explained in the literature. See, for example, Maniatis, Fritsch & Sambrook, MOLECULAR CLONING: A LABORATORY MANUAL, Cold Spring Harbor Laboratory Press (1982); Sambrook, Fritsch & Maniatis, MOLECULAR CLONING: A LABORATORY MANUAL, Second Edition, Cold Spring Harbor Laboratory Press (1989); Ausubel, et al., CURRENT PROTOCOLS IN MOLECULAR BIOLOGY, John Wiley & Sons (1987, 1988, 1989, 1990, 1991, 1992, 1993, 1994, 1995, 1996); Gait (ed.), OLIGONUCLEOTIDE SYNTHESIS: A PRACTICAL APPROACH, IRL Press (1984); Eckstein (ed.), OLIGONUCLEOTIDES AND ANALOGUES: A PRACTICAL APPROACH, IRL Press (1991).

Modified oligonucleotides wherein one or more purine bases (i.e., adenine and/or guanine) are substituted by their pyrazolo[3,4-d]pyrimidine analogues form stronger hybrids (i.e., duplexes) than those formed by unmodified oligonucleotides. Hybridization strength is generally assessed by determination of the melting temperature ($T_m$) of a hybrid duplex. This is accomplished by exposing a duplex in solution to gradually increasing temperature and monitoring the denaturation of the duplex, for example, by absorbance of ultraviolet light, which increases with the unstacking of base pairs that accompanies denaturation. $T_m$ is generally defined as the temperature midpoint of the transition from a fully duplex structure to complete denaturation (i.e., formation of two isolated single strands). Hybrids formed by oligonucleotides in which one or more purine residues are substituted by pyrazolo[3,4-d]pyrimidines have a higher ($T_m$) than those formed by unsubstituted oligonucleotides.

At the same time, modified oligonucleotides wherein one or more purine bases are substituted by pyrazolo[3,4-d] pyrimidines possess enhanced abilities for mismatch discrimination, compared to unsubstituted oligonucleotides. Without wishing to be bound by any particular theory, it is likely that one contribution to the enhanced discriminatory ability of pyrazolo[3,4-d]pyrimidine-modified oligonucleotides stems from the decreased tendency for a pyrazolo[3,4-d]pyrimidine base to participate in self-pairing or to pair with a non-standard base-pairing partner (i.e., whereas G is capable of base-pairing with G and T, ppG-G and ppG-T base pairs are much less likely).

Structure and Synthesis of Pyrazolo[3,4-d] Pyrimidine Nucleotides

In preferred embodiments of the modified oligonucleotides of the invention all, or substantially all, guanine-containing nucleotide units are replaced by a 6-amino-1H-pyrazolo[3,4-d]pyrimidin-4(5H)-one containing nucleotide (ppG). A ppG-containing portion of an oligonucleotide is illustrated in Formula 1. In less preferred embodiments not necessarily all, but nevertheless several guanine-containing nucleotide units are replaced by ppG.

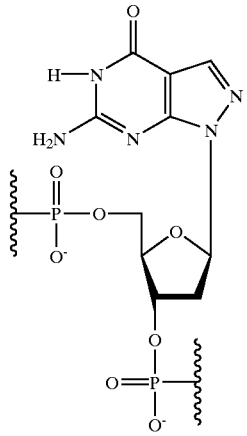

Formula 1

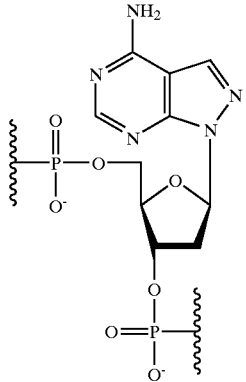

Formula 2

Optionally adenine containing nucleotide units of the oligonucleotide can also be replaced by the corresponding pyrazolo[3,4-d]pyrimidine analog, to wit: by 4-amino-1H-pyrazolo[3,4-d]pyrimidine. The nucleotide unit containing this adenine analog is termed ppA, and a ppA-containing portion of the oligonucleotide is illustrated in Formula 2. Thus, oligonucleotides where at least one guanine base has been replaced with ppG and which include no ppA analogue at all, as well as oligonucleotides which in addition to ppG also have some, or possibly all adenines replaced by ppA, as well as oligonucleotides which comprise at least one ppA analogue but no ppG, are within the scope of the invention.

The 2-deoxy-β-D-ribofuranosides of ppG and ppA, namely 6-amino-1-(2'-deoxy-β-D-erythro-pentofuranosyl- (1H)-pyrazolo[3,4-d]pyrimidin-4-5(H)-one and 4-amino-1-(2'-deoxy-β-D-erythropentofuranosyl-1H-pyrazolo[3,4-d]pyrimidine are synthesized and the corresponding activated phosphorous-containing analogs (phosphoramidites) suitable for oligonucleotide synthesis in a state-of-the-art automatic oligonucleotide synthesizer, are obtained in accordance with the literature procedures of Seela et al. (1986a) *Helvetica Chimica Acta* 69:1602–1613; Seela et al. (1988a) *Helvetica Chimica Acta* 71:1191–1198; Seela et al. (1988b) *Helvetica Chimica Acta* 71:1813–1823; and Seela et al. (1989) *Nucleic Acids Research* 17:901–910. Each of these publications is specifically incorporated herein by reference.

As a still further optional modification of the bases present in the modified oligonucleotides of the invention, the pyrazolo[3,4-d]pyrimidine 1H-pyrazolo[3,4-d]pyrimidin-4 (5H)-one (ppI) can replace one or more purine bases. ppI and the corresponding nucleosides and nucleotides can be obtained by methods related to those described. Seela et al. (1986b) *Liebigs. Ann. Chem.*: 1213–1221; Seela et al. (1986a), supra; Seela et al. (1988a), supra; Seela et al. (1988b), supra; and Seela et al. (1989), supra.

In the presently preferred embodiments of the modified oligonucleotides of the invention the sugar or glycosidic moieties are 2-deoxyribofuranosides, and all internucleotide linkages are the naturally occurring phosphodiester linkages. In alternative embodiments however, instead of 2-deoxy-β-D-ribofuranose, other sugars, for example, β-D-ribofuranose may be present. In addition, β-D-ribofuranose may be present wherein the 2-OH of the ribose moiety is alkylated with a $C_{1-6}$ alkyl group (2-(O—$C_{1-6}$ alkyl) ribose) or with a $C_{2-6}$ alkenyl group (2-(O—$C_{2-6}$ alkenyl) ribose), or is replaced by a fluoro group (2-fluororibose). Any sugar moiety compatible with hybridization of the oligonucleotide can be used, such as are known to those of skill in the art.

In a preferred embodiment, the sugar-phosphate backbone of the modified oligonucleotides of the present invention comprises phosphodiester bonds, as are found in naturally-occurring nucleic acids. However, the sugar-phosphate backbone can also comprise any structure that is compatible with hybridization of the oligonucleotide including, but not limited to, α-D-arabinofaranosides, α-2'-deoxyribofuranosides or 2',3'-dideoxy-3'-aminoribofuranosides. Oligonucleotides containing α-D-arabinofuranosides can be obtained in accordance with the teachings of U.S. Pat. No. 5,177,196, the disclosure of which is expressly incorporated herein by reference. Oligonucleotides containing 2',3'-dideoxy-3'aminoribofuranosides can be obtained in accordance with the method of Chen et al. (1995) *Nucleic Acids Res.* 23:2661–2668, expressly incorporated herein by reference. The phosphate backbone of the modified oligonucleotides of the invention may also be modified so that the oligonucleotides contain phosphorothioate linkages and/or methylphosphonates. Additional backbone modifications are known to those of skill in the art.

The modified oligonucleotides of the present invention can also comprise additional pendant groups such as, for example, intercalators, lipophilic groups, minor groove binders, reporter groups, chelating agents and cross-linking agents attached to one or more of the internally located nucleotide bases, to the 3', to the 5' end, to both ends, or can have such pendant groups attached both internally and at one or both ends. The nature and attachment of intercalator, lipophilic groups, minor grove binders, reporter groups, chelating agents and cross-linking agents to oligonucleotides are presently well known in the state-of-the-art, and are described, for example, in U.S. Pat. Nos. 5,512,667, 5,419,966 and in the publication WO 96/32496, which are incorporated herein by reference. The oligonucleotides of the invention can also have a relatively low molecular weight "tail moiety" attached either at the 3' or 5' end, or at both ends. By way of example a tail molecule can be a phosphate, a phosphate ester, an alkyl group, an aminoalkyl group, or a lipophilic group. The tail moiety can also link the intercalators, lipophilic groups, minor groove binders, reporter groups, chelating agents and cross-linking finctionalities to the oligonucleotides of the invention.

The nature of tail moieties and methods for obtaining oligonucleotides with various tail moieties are also described in the above-referenced U.S. Pat. Nos. 5,512,667 and 5,419,966.

In a preferred embodiment, modified oligonucleotides of the invention containing ppG substituted for guanine and/or ppA substituted for adenine also comprise a conjugated minor groove binder (MGB). Optimal single-nucleotide mismatch discrimination is obtained using MGB-conjugated oligonucleotides containing ppG in place of guanine, as shown in Examples 4 and 5, infra. Preferred MGB moieties include the trimer of 3-carbamoyl-1,2-dihydro-(3H)-pyrrolo [3,2-e]indole-7-carboxylate ($CDPI_3$) and the pentamer of N-methylpyrrole-4-carbox-2-amide ($MPC_5$). Additional MGB moieties that will find use in the practice of the present invention are disclosed in co-owned U.S. Pat. No. 5,801,155, the disclosure of which is hereby incorporated herein by reference.

Reactive precursors of pyrazolo[3,4-d]pyrimidines can be obtained following procedures described supra, and these precursors can be used in techniques of automated oligonucleotide synthesis. Such techniques are routine and well-known to those of skill in the art.

Methods of Use of the Invention

The present invention provides modified oligonucleotides having new and surprising properties of superior mismatch discrimination, compared to unmodified oligonucleotides. Modifted oligonucleotides of the invention are used as probes, wherein their hybridization to a target sequence is detected, or as primers, wherein their hybridization to a target sequence is followed by polynucleotide synthesis initiated from the 3' terminus of the modified oligonucleotide, and the synthesized product (i.e., the extension product) is detected.

A target sequence refers to a nucleotide sequence which comprises a site of hybridization for a probe or a primer. Target sequences can be found in any nucleic acid including, but not limited to, genomic DNA, cDNA and RNA, and can comprise a wild-type gene sequence, a mutant gene sequence, a non-coding sequence, a regulatory sequence, etc. A target sequence will generally be less than 100 nucleotides, preferably less than 50 nucleotides, and most preferably, less than 21 nucleotides in length.

Oligonucleotides are short polymers of nucleotides, generally less than 200 nucleotides, preferably less than 150 nucleotides, more preferably less than 100 nucleotides, more preferably less than 50 nucleotides and most preferably less than 21 nucleotides in length. Polynucleotides are generally considered, in the art, to comprise longer polymers of nucleotides than do oligonucleotides, although there is an art- recognized overlap between the upper limit of oligonucleotide length and the lower limit of polynucleotide length. With respect to the present invention, "oligonucleotide" generally refers to a nucleic acid, usually comprising a detectable label, that is used as a probe or as a primer; while polynucleotide refers to a nucleic acid containing a target sequence. Consequently, for the purposes of the present invention, the terms "oligonucleotide" and "polynucleotide" shall not be considered limiting with respect to polymer length.

Hybridization of probes and/or primers to target sequences proceeds according to well-known and art-recognized base-pairing properties, such that adenine base-pairs with thymine or uracil, and guanine base-pairs with cytosine. The property of a nucleotide that allows it to base-pair with a second nucleotide is called complementarity. Thus, adenine is complementary to both thymine and uracil, and vice versa; similarly, guanine is complementary to cytosine and vice versa. An oligonucleotide which is complementary along its entire length with a target sequence is said to be perfectly complementary, perfectly matched, or fully complementary to the target sequence, and vice versa. An oligonucleotide and its target sequence can have related sequences, wherein the majority of bases in the two sequences are complementary, but one or more bases are noncomplementary, or mismatched. In such a case, the sequences can be said to be substantially complementary to one another. If the sequences of an oligonucleotide and a target sequence are such that they are complementary at all nucleotide positions except one, the oligonucleotide and the target sequence have a single nucleotide mismatch with respect to each other.

The modified nucleotides of the invention retain the base-pairing specificity of their naturally-occurring analogues; i.e., ppG is complementary to cytosine, while ppA is complementary to thymine and uracil. The ppG and ppA analogues have a reduced tendency for so-called "wobble" pairing with non-complementary bases, compared to guanine and adenine.

Conditions for hybridization are well-known to those of skill in the art and can be varied within relatively wide limits. Hybridization stringency refers to the degree to which hybridization conditions disfavor the formation of hybrids containing mismatched nucleotides, thereby promoting the formation of perfectly matched hybrids or hybrids containing fewer mismatches; with higher stringency correlated with a lower tolerance for mismatched hybrids. Factors that affect the stringency of hybridization include, but are not limited to, temperature, pH, ionic strength, and concentration of organic solvents such as formamide and dimethylsulfoxide. As is well known to those of skill in the art, hybridization stringency is increased by higher temperatures, lower ionic strengths, and lower solvent concentrations. See, for example, Ausubel et al., supra; Sambrook et al., supra; M. A. Innis et al. (eds.) PCR Protocols, Academic Press, San Diego, 1990; B. D. Hames et al. (eds.) Nucleic Acid Hybridisation: A Practical Approach, IRL Press, Oxford, 1985; and van Ness et al., (1991)*Nucleic Acids Res.* 19:5143–5151.

Thus, in the formation of hybrids (duplexes) between an oligonucleotide and its target sequence, the oligonucleotide is incubated in solution, together with a polynucleotide containing the target sequence, under conditions of temperature, ionic strength, pH, etc, that are favorable to hybridization, i.e., under hybridization conditions. Hybridization conditions are chosen, in some circumstances, to favor hybridization between two nucleic acids having perfectly-matched sequences, as compared to a pair of nucleic acids having one or more mismatches in the hybridizing sequence. In other circumstances, hybridization conditions are chosen to allow hybridization between mismatched sequences, favoring hybridization between nucleic acids having fewer mismatches.

The degree of hybridization of an oligonucleotide to a target sequence, also known as hybridization strength, is determined by methods that are well-known in the art. A preferred method is to determine the $T_m$ of the hybrid duplex. This is accomplished, as described supra, by subjecting a duplex in solution to gradually increasing temperature and monitoring the denaturation of the duplex, for example, by absorbance of ultraviolet light, which increases with the unstacking of base pairs that accompanies denaturation. $T_m$ is generally defmed as the temperature midpoint of the transition in ultraviolet absorbance that accompanies denaturation. Alternatively, if $T_m$s are known, a hybridization temperature (at fixed ionic strength, pH and solvent concentration) can be chosen that is below the $T_m$ of the desired duplex and above the $T_m$ of an undesired duplex. In this case, determination of the degree of hybridization is accomplished simply by testing for the presence of hybridized probe.

If a probe comprises a detectable label, assays for hybridized probe are usually designed to detect the presence of label in duplex material. This can be accomplished, for example, by specifically selecting duplex material, specifically destroying single-stranded material, or utilizing some combination of these methods. For example, hybridization reaction mixtures can be subjected to high-stringency conditions and/or single strand-specific nucleases; or duplexes can be purified by affinity techniques specific for double-stranded, as opposed to single-stranded, nucleic acids. In a preferred embodiment of the invention, duplexes are detected by release of label from a probe under conditions in which label is released only when the probe is in a duplex.

Detectable labels or tags suitable for use with nucleic acid probes are well-known to those of skill in the art and include, but are not limited to, radioactive isotopes, chromophores, fluorophores, chemiluminescent and electrochemiluminescent agents, magnetic labels, immunologic labels, ligands and enzymatic labels. Suitable labels also include mass labels and those used in deconvolution of combinatorial chemistry libraries, for example, tags that can be recognized by high performance liquid chromatography (HPLC), gas chromatography, mass spectrometry, etc.

Methods for labeling of oligonucleotides are well-known to those of skill in the art and include, for example, chemical and enzymatic methods. By way of example, methods for incorporation of reactive chemical groups into oligonucleotides, at specific sites, are well-known to those of skill in the art. Oligonucleotides containing a reactive chemical group, located at a specific site, can be combined with a label attached to a complementary reactive group (e.g., an oligonucleotide containing a nucleophilic reactive group can be reacted with a label attached to an electrophilic reactive group) to couple a label to a probe by chemical techniques. Exemplary labels and methods for attachment of a label to an oligonucleotide are described, for example, in U.S. Pat. No. 5,210,015; Kessler (ed.), *Nonradioactive Labeling and Detection of Biomolecules*, Springer-Verlag, Berlin, 1992; Kricka (ed.) *Nonisotopic DNA Probe Techniques*, Academic Press, San Diego, 1992; Howard (ed.) *Methods in Nonradioactive Detection*, Appleton & Lange, Norwalk, 1993. Non-specific chemical labeling of an oligonucleotide can be achieved by combining the oligonucleotide with a chemical that reacts, for example, with a particular functional group of a nucleotide base, and simultaneously or subsequently reacting the oligonucleotide with a label. See, for example, Draper et al. (1980) *Biochemistry* 19:1774–1781. Enzymatic incorporation of label into an oligonucleotide can be achieved by conducting enzymatic modification or polymerization of an oligonucleotide using labeled precursors, or by enzymatically adding label to an already-existing oligonucleotide. See, for example, U.S. Pat. No. 5,449,767. Examples of modifying enzymes include, but are not limited to, DNA polymerases, reverse transcriptases, RNA polymerases, etc. Examples of enzymes which are able to add label to an already-existing oligonucleotide include, but are not limited to, kinases, terminal transferases, ligases, glycosylases, etc.

If an oligonucleotide is capable of acting as a primer, the degree of hybridization of the oligonucleotide can also be determined by measuring the levels of the extension product of the primer. In the case, either the primer can be labeled, or one or more of the precursors for polymerization (normally nucleoside triphosphates) can be labeled. Extension product can be detected, for example, by size (e.g., gel electrophoresis), affinity methods, or any other technique known to those of skill in the art.

Nucleotide monomers containing one or more reactive groups can be introduced into an oligonucleotide during automated synthesis; and these nucleotides can be used as points of label attachment. See Example 1, infra. Also, pyrazolo[3,4-d]pyrimidines containing linker arms can be incorporated into oligonucleotides by automated synthesis and serve as sites for attachment of various labels. See Example 1, infra and WO90/14353.

In certain embodiments of the present invention, oligonucleotides comprising fluorescent labels (fluorophores) and/or fluorescence quenching agents are used. In a preferred embodiment, an oligonucleotide contains both a fluorophore and a quenching agent. Fluorescent labels include, but are not limited to, fluoresceins, rhodamines, cyanines, phycoerythrins, and other fluorophores as are known to those of skill in the art. Quenching agents are those substances capable of absorbing energy emitted by a fluorophore so as to reduce the amount of fluorescence emitted (i.e., quench the emission of the fluorescent label). Different fluorophores are quenched by different quenching agents. In general, the spectral properties of a particular fluorophore/quenching agent pair are such that one or more absorption wavelengths of the quencher overlaps one or more of the emission wavelengths of the fluorophore. A preferred fluorophore/quencher pair is fluorescein/tetramethylrhodamine; additional fluorophore/quencher pair can be selected by those of skill in the art by comparison of emission and excitation wavelengths according to the properties set forth above.

For use in amplification assays conducted at elevated temperatures, such as a polymerase chain reaction, or other procedures utilizing thermostable enzymes, the label is stable at elevated temperatures. For assays involving polymerization, the label is such that it does not interfere with the activity of the polymerizing enzyme. Label can be present at the 5' and/or 3' end of the oligonucleotide, and/or can also be present internally. The label can be attached to any of the base, sugar or phosphate moieties of the oligonucleotide, or to any linking group that is itself attached to one of these moieties.

Exemplary Applications

The methods and compositions of the present invention can be used with a variety of techniques, both currently in use and to be developed, in which hybridization of an oligonucleotide to a target sequence in another nucleic acid is involved. These include, but are not limited to, 1) techniques in which hybridization of an oligonucleotide to a target sequence is the endpoint; 2) techniques in which hybridization of one or more oligonucleotides to a target sequence precedes one or more polymerase-mediated elongation steps which use the oligonucleotide as a primer and the target nucleic acid as a template; 3) techniques in which hybridization of an oligonucleotide to a target sequence is used to block extension of another primer; 4) techniques in which hybridization of an oligonucleotide to a target sequence is followed by hydrolysis of the oligonucleotide to release an attached label; and 5) techniques in which two or more oligonucleotides are hybridized to a target sequence and interactions between the multiple oligonucleotides are measured.

Hybridization Probes

In one aspect of the present invention, one or more modified oligonucleotides are used as probe(s) to identify a target sequence in a nucleic acid by assaying hybridization between the probe(s) and the nucleic acid. A probe can be labeled with any detectable label, or it can have the capacity to become labeled either before or after hybridization, such as by containing a reactive group capable of association with a label or by being capable of hybridizing to a secondary labeled probe, either before or after hybridization to the target. Conditions for hybridization of nucleic acid probes are well-known to those of skill in the art. See, for example, Sambrook et al., supra; Ausubel et al., supra; Innis et al., supra; Hames et al., supra; and van Ness et al., supra.

Hybridization can be assayed (i.e., hybridized nucleic acids can be identified) by distinguishing hybridized probe from free probe by one of several methods that are well-known to those of skill in the art. These include, but are not limited to, attachment of target nucleic acid to a solid support, either directly or indirectly (by hybridization to a second, support-bound probe) followed by direct or indirect hybridization with probe, and washing to remove unhybridized probe; determination of nuclease resistance; buoyant density determination; affinity methods specific for nucleic acid duplexes (e.g., hydroxyapatite chromatography); interactions between multiple probes hybridized to the same target nucleic acid; etc. See, for example, Falkow et al., U.S. Pat. No. 4,358,535; Urdea et al., U.S. Pat. Nos. 4,868,105 and 5,124,246; Freifelder, *Physical Biochemistry*, Second Edition, W. H. Freeman & Co., San Francisco, 1982; Sambrook, et al., supra; Ausubel et al., supra; Hames et al., supra; and other related references.

The modified oligonucleotides disclosed herein are particularly useful for distinguishing one among a group of related target sequences. Related target sequences are those whose sequences differ at one or more nucleotide positions, but which are complementary over a majority of their length. In a preferred embodiment of the invention, modified oligonucleotides are able to distinguish related target sequences which differ by only a single nucleotide. For example, it is possible to select hybridization conditions in which perfectly-matched sequences form detectable hybrids, but two sequences having a single-nucleotide mismatch do not form detectable hybrids. See Example 5, infra.

Amplification Primers

Amplification procedures are those in which many copies of a target nucleic acid sequence are generated, usually in an exponential fashion, by sequential polymerization and/or ligation reactions. Many amplification reactions, such as polymerase chain reactions (PCR), utilize reiterative primer-dependent polymerization reactions. A primer is a nucleic acid that is capable of hybridizing to a second, template nucleic acid and that, once hybridized, is capable of being extended by a polymerizing enzyme (in the presence of nucleotide substrates), using the second nucleic acid as a template. Polymerizing enzymes include, but are not limited to, DNA and RNA polymerases and reverse transcriptases, etc. Thermostable polymerases are preferred in most amplification reactions. Conditions favorable for polymerization by different polymerizing enzymes are well-known to those of skill in the art. See, for example, Sambrook et al., supra; Ausubel, et al., supra; Innis et al., supra. Generally, in order to be extendible by a polymerizing enzyme, a primer must have an unblocked 3'-end, preferably a free 3' hydroxyl group. The product of an amplification reaction is an extended primer, wherein the primer has been extended by a polymerizing enzyme.

Thus, in one embodiment of the invention, the methods and compositions disclosed and claimed herein are useful in improved amplification reactions such as PCR. See, e.g., U.S. Pat. Nos. 4,683,202; 4,683,195 and 4,800,159. The practice of the invention will be especially useful in situations in which it is desired to selectively amplify a particular sequence which differs from undesired sequences by one or a small number of nucleotides.

The improvements provided by the present invention are applicable to any type of assay or procedure in which PCR or a related amplification technique is used, including, but not limited to, priming with allele-specific oligonucleotides (ASOs), fragment length polymorphism analysis, single nucleotide polymorphism (SNP) analysis and microsatellite analysis, for example. These and other techniques are useful in gene mapping, in the identification and screening of disease-related genes, and in pharmacogenetics, to name just a few applications.

Assays Utilizing Labeled Probes; Including Hydrolyzable Probe Assays

Additional uses for modified oligonucleotides are found in assays in which a labeled probe is hybridized to a target sequence and/or an extension product comprising a target sequence, and a change in the physical state of the label is effected as a consequence of hybridization. By way of example, one assay of this type, the hydrolyzable probe assay, takes advantage of the fact that many polymerizing enzymes, such as DNA polymerases, possess intrinsic 5'-3' exonucleolytic activities. Accordingly, if a probe is hybridized to a sequence that can serve as a template for polymerization (for instance, if a probe is hybridized to a region of DNA located between two amplification primers, during the course of an amplification reaction), a polymerizing enzyme that has initiated polymerization at an upstream amplification primer is capable of exonucleolytic digestion of the probe. Any label attached to such a probe will be released as a consequence of the exonucleolytic digestion of the probe. Released label is separated from labeled probe and detected by methods well-known to those of skill in the art, depending on the nature of the label. For example, radioactively labeled fragments can be separated by thin-layer chromatography and detected by autoradiography; while fluorescently-labeled fragments can be detected by irradiation at the appropriate excitation wavelengths with observation at the appropriate emission wavelengths. See, e.g., U.S. Pat. No. 5,210,015.

In a preferred embodiment, a probe comprising a modified oligonucleotide contains both a fluorescent label and a quenching agent, which quenches the fluorescence emission of the fluorescent label. In this case, the fluorescent label is not detectable until its spatial relationship to the quenching agent has been altered, for example by exonucleolytic release of the fluorescent label from the probe. Thus, prior to hybridization to its target sequence, the dual fluorophore/quencher labeled probe does not emit fluorescence. Subsequent to hybridization of the fluorophore/quencher-labeled probe to its target, it becomes a substrate for the exonucleolytic activity of a polymerizing enzyme which has initiated polymerization at an upstream primer. Exonucleolytic degradation of the probe releases the fluorescent label from the probe, and hence from the vicinity of the quenching agent, allowing detection of a fluorescent signal upon irradiation at the appropriate excitation wavelengths. This method has the advantage that released label does not have to be separated from intact probe. Multiplex approaches utilize multiple probes, each of which is complementary to a different target sequence and carries a distinguishable label, allowing the assay of several target sequences simultaneously.

This type of assay is becoming increasingly important, especially in clinical applications, because it is. a homogeneous assay (i.e., no product separation steps are required for analysis) in which the results can be monitored in real time. See, for example, Wittwer et al. (1997) *BioTechniques* 22:130–138. Rapid, fluorescence-based molecular assays find use in, for example, real-time surgical and therapeutic applications, as well.

The enhanced ability of modified oligonucleotides to discriminate between related target sequences will facilitate the use of hydrolyzable probe assays in the identification of, for example, single-nucleotide polymorphisms and the like. Examples 4 and 5, infra, disclose the use of modified oligonucleotides in a hydrolyzable probe assay.

Additional assays involving the principles of fluorescence quenching will be apparent to those skilled in the art, as will the advantages of using modified oligonucleotides in such assays. It will also be clear to those of skill in the art that fluorescently-labeled modified oligonucleotides provide improvements in discriminatory power in the practice of all types of hybridization assays.

Fluorescence Energy Transfer

In further embodiments of the invention, modified oligonucleotides are used in various techniques which involve multiple fluorescently-labeled probes. In some of these assays, fluorescence and/or changes in properties of a fluorescent label are used to monitor hybridization. For example, fluorescence resonance energy transfer (FRET) has been used as an indicator of oligonucleotide hybridization. In one embodiment of this technique, two probes are used, each containing a different fluorescent label. One of the labels is a fluorescence donor, and the other is a fluorescence acceptor, wherein the emission wavelengths of the fluorescence donor overlap the absorption wavelengths of the fluorescence acceptor. The sequences of the probes are selected so that they hybridize to adjacent regions of a target sequence, thereby bringing the fluorescence donor and the fluorescence acceptor into close proximity, if target is present. In the presence of target nucleic acid, irradiation at wavelengths corresponding to the absorption wavelengths of the fluorescence donor will result in emission from the fluorescence acceptor. These types of assays have the advantage that they are homogeneous assays, providing a positive signal without the necessity of removing unreacted probe. For further details and additional examples, see, for example, European Patent Publication 070685; and Cardullo, et al. (1988) *Proc. Natl. Acad. Sci. USA* 85: 8790–8794.

Additional embodiments of the present invention will be found in these and related techniques in which interactions between two different oligonucleotides that are hybridized to the same target nucleic acid are measured. The selection of appropriate fluorescence donor/fluorescence acceptor pairs will be apparent to one of skill in the art, based on the principle that, for a given pair, the emission wavelengths of the fluorescence donor will overlap the absorption wavelengths of the fluorescence acceptor. The enhanced ability of modified oligonucleotides to distinguish among related target sequences facilitates the use of FRET-based techniques in the identification of single-nucleotide polymorphisms and the like.

Assays Involving Oligonucleotide Ligation

Modified oligonucleotides are useful in assays in which two or more oligonucleotides, complementary to adjacent sites on a target nucleic acid, are hybridized to adjacent sites on the target nucleic acid and ligated to one another. See, for example, European Patent Publication 320,308; European Patent Publication 336,731; and U.S. Pat. No. 4,883,750. Conditions for ligation are well-known to those of skill in the art. See, for example, Sambrook et al., supra; Ausubel, et al., supra; Innis et al., supra. Ligated nucleic acids can be identified, for example, by an increase in size of the product compared to the starting oligonucleotides. As in the case with hybridization assays, use of modified oligonucleotides in assays involving ligation allows more efficient discrimination among related target sequences; particularly between perfect hybrids and single-base mismatches, which is especially important in oligonucleotide ligation assays.

cDNA Synthesis

Synthesis of cDNA, as commonly practiced, utilizes a reverse transcriptase enzyme to copy a mRNA template into cDNA. The primer for reverse transcription is normally oligodeoxythymidylate, which is complementary to the polyadenylate tail found at the 3' end of most mRNA molecules. However, cDNA synthesis rarely proceeds all the way to the 5' terminus of the template MRNA molecule. Thus, most cDNA libraries are enriched for sequences near the 3' ends of mRNAs and deficient in sequences near the 5' end. Consequently, to obtain a complete cDNA representation of a mRNA sequence, one or more additional synthesis reactions, primed at internal regions of the mRNA template, must be conducted. Modified oligonucleotides can be in these internal priming steps, allowing discrimination between closely related mRNA sequences, such as might be found in different members of a gene family.

In addition, synthesis of cDNA is often conducted under conditions of low stringency, to promote the hybridization of the oligodeoxythymidylate primer to the polyadenylate tail. Under such conditions, MRNA molecules are known to readily adopt intramolecular secondary structures, which can act as blocks to elongation by reverse transcriptase, leading to production of short, partial cDNA molecules. cDNA synthesis using modified oligonucleotides as primers can, by contrast, proceed under more stringent conditions, wherein secondary structure in the mRNA template is minimized, leading to the synthesis of longer cDNA products.

Nucleic Acid Sequencing

In one embodiment of the invention, a collection of all possible n-mer oligonucleotides (where n is an integer less than about 10) are used in a hydrolyzable probe assay to determine a nucleotide sequence. Each oligonucleotide is uniquely labeled and analysis of released label indicates which of the oligonucleotides has hybridized to the target sequence. Alignment of the sequences of the oligonucleotides which have hybridized provides the nucleotide sequence. Modified oligonucleotides, with heightened discriminatory properties, are particularly suitable for use in this technique.

Modified oligonucleotides are also useful in primer-dependent methods of DNA sequencing, such as the chain-termination method and its derivatives, originally described by Sanger et al. (1977) *Proc. Natl. Acad. Sci. USA* 74:5463–5467. Use of modified oligonucleotides in chain-termination sequencing enables a greater degree of mismatch discrimination during sequencing, providing, for example, improved means for distinguishing between two or more closely-related sequences.

Oligonucleotide Arrays

In another embodiment of the present invention, modified oligonucleotides are used in procedures which utilize arrays of oligonucleotides, such as sequencing by hybridization and array-based analysis of gene expression. In sequencing by hybridization, an ordered array of oligonucleotides of different known sequences is used as a platform for hybridization to one or more test polynucleotides, nucleic acids or nucleic acid populations. Determination of the oligonucleotides which are hybridized and alignment of their known sequences allows reconstruction of the sequence of the test polynucleotide. Alternatively, oligonucleotides comprising the wild-type sequence and all possible mutant sequences for a given region of a gene of interest can be placed on an array. Exposure of the array to DNA or RNA from a subject or biological specimen, under hybridization conditions, allows determination of wild-type or mutant status for the gene of interest. See, for example, U.S. Pat. Nos. 5,492,806; 5,525,464; 5,556,752; and PCT Publications WO 92/10588 and WO 96/17957. Both of these techniques require discrimination between related sequences, especially at the single-nucleotide level; hence, the enhanced discriminatory properties of the modified oligonucleotides of the invention will provide improvements in these techniques. Materials for construction of arrays include, but are not limited to, nitrocellulose, glass, silicon wafers, optical fibers and other materials suitable for construction of arrays such as are known to those of skill in the art.

An additional application of the present invention to array technology is in the examination of patterns of gene expression in a particular cell or tissue. In this case, oligonucleotides or polynucleotides corresponding to different genes are arrayed on a surface, and a nucleic acid sample from a particular cell or tissue type, for example, is incubated with the array under hybridization conditions. Detection of the sites on the array at which hybridization occurs allows one to determine which oligonucleotides have hybridized, and hence which genes are active in the particular cell or tissue from which the sample was derived.

Array methods can also be used for identification of mutations, where wild-type and mutant sequences are placed in an ordered array on a surface. Hybridization of a polynucleotide sample to the array under stringent conditions, and determination of which oligonucleotides in the array hybridize to the polynucleotide, allows determination of whether the polynucleotide possesses the wild-type or the mutant sequence. Since many mutant sequences of clinically-relevant genes differ from their wild-type counterpart at only one or a few nucleotide positions, the enhanced discriminatory powers of the modified oligonucleotides of the invention will provide improvements in mutation detection.

In all of the above-mentioned applications of array technology, the increased discriminatory abilities of modified oligonucleotide provide significant improvements in sensitivity and resolving power.

EXAMPLES

The following examples are intended to illustrate, not to limit the invention.

In the hydrolyzable probe assay, a labeled probe is added to a PCR reaction. The probe is complementary to a region between the two PCR primers and is labeled with two fluorophores, one of which quenches the fluorescence of the other. The probe is designed to hybridize to its complementary target sequence on one of the PCR product strands at or above the strand extension temperature typically used in PCR (55–75° C.). The polymerizing enzymes normally used in PCR (Taq polymerase in particular) possess an intrinsic 5'-exonuclease activity. During synthesis of new strands in the extension stage of the PCR reaction, this 5'-exonuclease activity will act on complementary strands bound to the template. If a probe, labeled as described above, is bound to the template, the 5'-exonuclease activity associated with the polymerizing enzyme will liberate the bound fluorophore. Once liberated, its fluorescence will no longer be quenched, and a fluorescent signal will be obtained. See, for example, U.S. Pat. No. 5,210,015; Livak et al. (1995) *PCR Meth. App.* 4:357–362; and Heid et al. (1996) *Genome Res.* 6:986–994.

Example 1

Preparation of Dual-labeled, MGB-conjugated Hydrolyzable Probes

Synthesis of oligonucleotide probes carrying a 5'-reporting dye [(3',6'-dipivaloylfluoresceinyl)-6-carboxamidohexyl]-1-O-(2-cyanoethyl)-(N,N-diisopropyl) -phosphoramidite (6-FAM) and 3'-CDPI$_3$-tail (Scheme 1). Oligonucleotides with a conjugated CDPI$_3$ tail were prepared on a 1 μmol scale using standard 3'-phosphoramidite chemistry on a CDPI$_3$-CPG support (~20–50 mg) Preparation of the CDPI$_3$-CPG support is disclosed in Lukhtanov et al. (1995) *Bioconj. Chem.* 6:418–426. Oligonucleotides lacking a conjugated MGB were synthesized by standard procedures. Synthesis was performed on an ABI 394 according to the protocol supplied by the manufacturer with one exception: 0.01 M (instead of the standard 0.1 M) iodine solution was utilized in the oxidation step to avoid iodination of the CDPI$_3$ moiety, when CDPI$_3$-conjugated oligonucleotides were being synthesized. An amino-linker for postsynthetic incorporation of the TAMRA dye (see below) was introduced near the 3'-end of the oligonucleotide by incorporating a protected aminopropyl ppG or aminopropyl ppA phosphoramidite (see co-owned, allowed U.S. patent application Ser. No. 08/334,490) in place of a G or A residue, respectively, at the desired step of automated oligonucleotide synthesis. To incorporate a FAM dye at the 5'-end of the probes, 5'-Fluorescein Phosphoramidite (6-FAM, Glen Research, Cat.#10-5901) was used at the last step in the synthesis of an oligonucleotide. After cleavage from the solid support and complete deprotection by ammonia treatment (30% ammonia, 12–15 hrs, 50° C.) reactions were filtered and dried by rotary evaporation. Probes containing a CDPI$_3$ tail were isolated by RP-HPLC on a 4.6×250 mm, C-18, Dynamax-300A column (Rainin) with a linear gradient of acetonitrile (0→60%, 20 min, 2 mL/min) in 0.1 M triethylammonium acetate buffer (pH 7.4). Fractions containing CDPI$_3$-tailed probe were concentrated with butanol to a volume of 60–100 μl in 1.5 ml plastic tubes, precipitated in 2% NaClO$_4$ (or LiClO$_4$, 1.5 mL) in acetone, washed with acetone, and dried in vacuo. The HPLC purified probes were either (i) used directly for incorporation of a TAMRA dye or (ii) additionally purified by 8% denaturing polyacrylamide gel electrophoresis (see below).
Post-synthetic Introduction of TAMRA Residue (Scheme 2).

An N-hydroxysuccinimide ester of Tetramethylrhodamine (TAMRA NHS Ester, Glen Research, Cat.#50-5910) was incorporated at an aminopropyl ppG or aminopropyl ppA residue of the 5'-FAM, 3'-CDPI$_3$-tailed oligonucleotide probes (synthesized as described above) using the protocol supplied by the manufacturer. The reaction solution was then saturated with urea (~400 μl) and loaded onto an 8% denaturing polyacrylamide gels (1.5×270 mm packet, 38×50 cm plate, Bio-Rad Laboratories; gel buffer contained 7 M urea, 2 mM EDTA, 90 mM Tris-borate, pH 8.3). Gel purification was performed at a constant power setting (100 Watts, 50–55° C.). The desired products of conjugation (ie., probes carrying 6-FAM, TAMRA, and CDPI$_3$ residues) were detected,by the TAMRA-specific color and cut out of the gel. Gel slices were incubated at 37° C. overnight in 4–6 ml of 100 mM Tris-HCl, 10 mM triethylammonium acetate, 1 mM EDTA, pH 7.8. Finally, the conjugates were isolated from the gel extract either by (i) reverse phase HPLC as described above or (ii) using MA-CLEAN C18 cartridges according to the protocol supplied by manufacturer (Alltech Associates, Inc.). In either case the probes were concentrated with butanol, precipitated in 2% NaClO$_4$ in acetone, washed with pure acetone, dried in vacuo, dissolved in 100–400 μl of water, and stored at –20° C.

Presence of the conjugated moieties in the oligonucleotide probes was confirmed by absorbance at specific UV and visible wavelengths. The following wavelengths were used: 255–265 nm for detection of nucleic acid, 350 nm for detection of CDPI$_3$, 460–480 nm for detection of 6-FAM, and 570 nm for detection of TAMRA.

Example 2

Target, Primer and Probe Sequences

Strategy

The target sequence is located in the *E. coli* supF gene contained in the plasmid pSP189 (FIG. 1, SEQ ID NO.: 1). See Parris et al. (1992) *Gene* 117:1–5. Binding sites for the primers used for amplification are indicated as Primer 1 and Primer 2, with Primer 1 having a sequence and polarity that is identical to that shown in FIG. 1, and Primer 2 having a sequence and polarity that is the reverse complement to that shown in FIG. 1. Three probes having overlapping sequences, each labeled with FAM at the 5'-end and with the quencher TAMRA at the 3'-end with were synthesized: a 12-mer, a 15-mer and an 18-mer. The 12-mer and 15-mer additionally contained a conjugated minor groove binder (CDPI$_3$) near the 3'-end of the oligonucleotide. Finally, each probe contained either normal guanine residues (indicated by G in the Tables) or all of its guanine residues were substituted with ppG (indicated by ppG in the Tables). These probes were used to determine the effect of substitution of ppG for G on hybridization strength and mismatch discrimination.

Primer Sequences

The forward amplification primer has the sequence:
5'-CTGGGTGAGCAAAAACAGGAAGGC-3' SEQ ID No.: 2
The reverse primer has the sequence:
5'-TGTGATGCTCGTCAGGGGGG-3' SEQ ID No.: 3

Sequences of Probes:
The 12-mer probe has the following sequence:
5'-TTCCCGAGCGGC SEQ ID NO.:4
The 15-mer probe has the following sequence:
5'-GGGTTCCCGAGCGGC SEQ ID NO.:5
The 18-mer probe has the following sequence:
5'-GTGGGGTTCCCGAGCGGC SEQ ID NO.:6

Template Sequences

The 18-nucleotide region of the template that is complementary to the probes used in this study was modified to generate a series of point mutations, as shown in FIG. 1.

Each of the mutant templates was used in a separate assay with each of the three probes. The mutant sequences within this region of the template were as follows, with the mismatched nucleotide indicated by bold underlining:

5'-GTGGGGTTCCCGAGCGGC (perfect match) SEQ ID NO.: 7

5'-GTGGAGTTCCCGAGCGGC (32 G-A mismatch) SEQ ID NO.: 8

5'-GTGGGGTTTCCGAGCGGC (36 C-T mismatch) SEQ ID NO.: 9

5'-GTGGGGTTGCCGAGCGGC (36 C-G mismatch) SEQ ID NO.: 10

5'-GTGGGGTTACCGAGCGGC (37 C-A mismatch) SEQ ID NO.: 11

5'-GTGGGGTTCTCGAGCGGC (37 C-T mismatch) SEQ ID NO.: 12

5'-GTGGGGTTCACGAGCGGC (39 C-A mismatch) SEQ ID NO.: 13

5'-GTGGGGTTCCCCAGCGGC (39 G-C mismatch) SEQ ID NO.: 14

5'-GTGGGGTTCCCGTGCGGC (40 A-T mismatch) SEQ ID NO.: 15

5'-GTGGGGTTCCCGAACGGC (41 G-A mismatch) SEQ ID NO.: 16

5'-GTGGGGTTCCCGACCGGC (41 G-C mismatch) SEQ ID NO.: 17

5'-GTGGGGTTCCCGAGCAGC (43 G-A mismatch) SEQ ID NO.: 18

5'-GTGGGGTTCCCGAGCTGC (43 G-T mismatch) SEQ ID NO.: 19

5'-GTGGGGTTCCCGAGCGTC (44 G-T mismatch) SEQ ID NO.: 20

Example 3

Hydrolyzable Probe Assay

Hydrolyzable probe assays with fluorescent monitoring were performed in an Idaho Technologies Light Cycler. Wittwer et al. (1997a) BioTechniques 22:130–138, and Wittwer et al. (1997b) BioTechniques 22:176–181. Each reaction mixture contained:

40 mM NaCl 20 mM Tris-Cl, pH 8.9

5 mM $MgSO_4$ 0.05% (w/v) Bovine Serum Albumin

125 µM each dATP, dGTP, dCTP, dTTP 0.5 µM each primer 0.5 µM probe 0.5 U/10 µL Taq Polymerase Cycling conditions were 40 cycles of 0 sec at 94° C. (i.e., temperature was raised to 94° C. and immediately lowered to the annealing/extension temperature), then 15 sec at the annealing/extension temperature (which varied from 55–75° C. in individual experiments; see below and in figure legends for details). Fluorescent output was expressed as the ratio of fluorescence at 515–560 nm (fluorescein) to that at 560–630 nm (rhodamine), as analyzed by the manufacturer's software that was provided with the light cycler.

Melting temperatures (Table 3) were determined on a Perkin Elmer λ2S UV/VIS spectrophotometer, equipped with a PTP-6 temperature controller, using the PECSS software package.

Example 4

Effect of ppG Substitution on $T_m$ and on Single Nucleotide Mismatch Discrimination Oligonucleotides of 12, 15 or 18 nucleotides, spanning the same target sequence region, were used as hydrolyzable probes and tested for hybridization to a perfectly-matched target sequence, and to different single nucleotide mismatched target sequences (FIG. 1). Each probe was tested with and without substitution of all G residues by ppG. The 12-mer and 15-mer oligonucleotides additionally contained a conjugated MGB. A common pair of primers was used to amplify the segment of the template containing the target sequence. Fluorescence values are given, in Table 1, for assays in which either the wild type sequence, to which the probe is perfectly matched (labeled "match" in the table), or one of the mismatched mutant sequences, is used as template. Table 1 shows the amount of fluorescent signal generated after 40 cycles of PCR, in arbitrary fluorescence units. This value provides an estimate of the number of copies of target present in the original sample (Wittwer et al, supra) and, for equivalent amounts of initial target, provides an approximate measure of the efficiency of the hydrolyzable probe in the assay. The results are presented in two ways. Table 1 shows the absolute fluorescence measured in the assay after 40 cycles of amplification. In Table 2, the fluorescence value (after 40 cycles) of each mismatched probe/template hybrid is given as a percentage of the value obtained for the perfectly matched hybrid.

Two advantages resulting from the use of the ppG substitution are evident from the data presented in Tables 1 and 2. First, the substitution of ppG for G in a probe enhances the intensity of the measured signal obtained with that probe. While the signal from any particular probe will depend on conditions used for the assay, the fact that addition of ppG to the probe always enhances the signal could imply that hybrids formed with ppG-containing oligonucleotides have higher $T_m$ values. Table 3 shows that this is indeed the case. In all cases tested, the $T_m$ for a hybrid containing a ppG-substituted oligonucleotide is 1–4° C. higher than that of a hybrid formed with an unsubstituted oligonucleotide.

The second advantage of using ppG-substituted oligonucleotides is that the presence of ppG in the probe significantly enhances single-nucleotide mismatch discrimination. When fluorescence obtained with a given probe/template pair is expressed as percentage of the fluorescence obtained in an assay with the perfectly-matched probe/template pair (Table 2), it can be seen that, in general, inclusion of ppG in place of G reduces the ratio of signal obtained from mismatched targets to signal obtained from a perfectly-matched target. Without wishing to be bound by any particular theory, it is suggested that the enhanced mismatch discrimination obtained with ppG-substituted oligonucleotides may be related to the propensity of guanine to form unusual base pairs (i.e., with bases other than cytosine), a property that ppG may not have.

Example 5

Effect of ppG Substitution on Single Nucleotide Mismatch Discrimination

FIG. 2 shows a time-course for fluorescence release in a hydrolyzable probe assay (as described in Example 3) when annealing/elongation was conducted at 72° C. with MGB-conjugated 15-mer probes. Although the perfect match (denoted "match" in the Figure) provides the highest level of signal, detectable signals are also obtained from many of the probes harboring a single-nucleotide mismatch with the target. However, if the assay is conducted under identical conditions except that all guanine residues in the MGB-conjugated oligonucleotide probes are replaced by ppG, generation of signal by probes containing a single-base mismatch is significantly reduced, while the amount of signal generated by the perfectly-matched probe is unaffected (FIG. 3). If, in addition, ppg-modified, MGB-conjugated, oligonucleotide probes are used in an assay in which the annealing/elongation temperature is raised to 75° C., generation of signal by probes with a single-base mismatch is completely suppressed, again with no effect on the level of signal generated by the perfectly-matched probe (FIG. 4).

Thus, the combination of MGB conjugation, substitution with pyrazolo[3,4-d]pyrimidine base analogues, and appropriate reaction conditions enable facile discrimination between a perfect-matched hybrid and a hybrid containing a single-nucleotide mismatch, at high stringency, allowing a heretofore unparalleled degree of specificity to be obtained in hybridization reactions with short oligonucleotides.

TABLE 1

Fluorescence release during amplification of the supF gene

| Sequence: | 12-mer, 68° C., +MGB | | 15-mer, 75° C., +MGB | | 18-mer, 68° C., −MGB | |
|---|---|---|---|---|---|---|
| | G | ppG | G | ppG | G | ppG |
| Match | 4.85 | 5.62 | 1.01 | 4.67 | 0.58 | 2.39 |
| 32 G-A | | | 0.12 | 0.55 | 0.04 | 0.17 |
| 36 C-T | 0.12 | 0.10 | 0.00 | 0.15 | 0.00 | 0.00 |
| 36 C-G | 0.02 | 0.00 | 0.00 | 0.09 | 0.00 | 0.00 |
| 36 C-A | 0.00 | 0.00 | 0.00 | 0.00 | 0.00 | 0.00 |
| 37 C-T | 0.05 | 0.05 | 0.02 | 0.05 | 0.01 | 0.03 |
| 37 C-A | 0.01 | 0.00 | 0.04 | 0.11 | 0.00 | 0.00 |
| 39 G-C | 0.03 | 0.00 | 0.02 | 0.05 | 0.07 | 0.02 |
| 40 A-T | 0.56 | 0.51 | 0.16 | 0.37 | 0.03 | 0.03 |
| 41 G-A | 0.18 | 0.01 | 0.06 | 0.33 | 0.05 | 0.03 |
| 41 G-C | 0.55 | 0.34 | 0.10 | 0.23 | 0.06 | 0.05 |
| 43 G-A | 0.12 | 0.05 | 0.29 | 0.24 | 0.06 | 0.04 |
| 43 G-T | 0.13 | 0.01 | 0.15 | 0.14 | 0.04 | 0.10 |
| 44 G-T | 0.57 | 0.63 | 0.65 | 0.24 | 0.13 | 0.23 |

TABLE 2

Fluorescence as a percentage of perfectly-matched probe for oligonucleotides ± ppG

| Sequence: | 12-mer + MGB, 68° C. | | 15-mer + MGB, 75° C. | | 18-mer − MGB, 68° C. | |
|---|---|---|---|---|---|---|
| | G | ppG | G | ppG | G | ppG |
| Match | 100 | 100 | 100 | 100 | 100 | 100 |
| 32 G-A | | | 11 | 12 | 6 | 7 |
| 36 C-T | 2 | 2 | 0 | 3 | 0 | 0 |
| 36 C-G | 0 | 0 | 0 | 2 | 0 | 0 |
| 36 C-A | 0 | 0 | 0 | 0 | 0 | 0 |
| 37 C-T | 1 | 1 | 2 | 1 | 1 | 1 |
| 37 C-A | 0 | 0 | 4 | 2 | 0 | 0 |
| 39 G-C | 1 | 0 | 2 | 1 | 12 | 1 |
| 40 A-T | 11 | 9 | 16 | 8 | 5 | 1 |
| 41 G-A | 4 | 0 | 6 | 7 | 9 | 1 |
| 41 G-C | 11 | 6 | 9 | 5 | 10 | 2 |
| 43 G-A | 3 | 1 | 29 | 5 | 11 | 1 |
| 43 G-T | 3 | 0 | 14 | 3 | 7 | 4 |
| 44 G-T | 12 | 11 | 64 | 5 | 23 | 10 |

TABLE 3

Melting temperatures of hybrids formed by MGB-conjugated 15-mer oligonucleotides ± ppG

| Sequence: | $T_m$ | | $\Delta T_m$ |
|---|---|---|---|
| | G | ppG | |
| Match | 71 | 74 | 3 |
| 32 G-A | 65 | 67 | 2 |
| 36 C-T | 62 | 65 | 3 |
| 36 C-G | 62 | 64 | 2 |
| 36 C-A | 66 | 67 | 1 |
| 37 C-T | 68 | 69 | 1 |
| 37 C-A | 71 | 73 | 2 |
| 39 G-C | 60 | 61 | 1 |
| 40 A-T | 60 | 64 | 4 |
| 41 G-A | 60 | 64 | 4 |
| 41 G-C | 60 | 63 | 3 |
| 43 G-A | 57 | 59 | 2 |
| 43 G-T | 59 | 61 | 2 |
| 44 G-T | 66 | 69 | 3 |

While the foregoing invention has been described in some detail by way of illustration and example for purposes of clarity of understanding, it will be apparent to those skilled in the art that various changes and modifications can be practiced without departing from the spirit of the invention. Therefore the foregoing descriptions and examples should not be construed as limiting the scope of the invention.

---

What is claimed is:

1. A method for detecting the presence of a target sequence in a plurality of polynucleotides, wherein the plurality of polynucleotides differ from one another by a single nucleotide within the target sequence, the method comprising the following steps:

(a) providing the plurality of polynucleotides which are to be tested for the presence of the target sequence;

(b) providing an oligonucleotide having a sequence that is substantially complementary to the target sequence, wherein one or more purine residues of the oligonucleotide are substituted by a pyrazolo[3,4-d]pyrimidine;

(c) incubating the plurality of polynucleotides and the oligonucleotide under hybridization conditions; and (d) identifying hybridized nucleic acids;
wherein the presence of hybridized nucleic acids is indicative of the presence of the target sequence in the plurality of polynucleotides.

2. The method according to claim 1, wherein the oligonucleotide further comprises a minor groove binding moiety.

3. The method according to claim 1 wherein the oligonucleotide is a primer comprising an extendible 3'-hydroxyl group.

4. The method according to claim 3, wherein hybridized nucleic acids are identified by extending the primer with a polymerizing enzyme.

5. The method according to claim 4 wherein the polymerizing enzyme is a thermostable enzyme.

6. The method according to claim 3, wherein the oligonucleotide is a primer in an amplification reaction.

7. The method according to claim 6, wherein the amplification reaction is a polymerase chain reaction.

8. A method for identifying a mutation in a target sequence of a gene of interest, the method comprising the following steps:

(a) providing a polynucleotide that comprises the target sequence, (b) providing an array of oligonucleotides of different sequences, wherein one or more purine residues in at least one of the oligonucleotides are substituted by a pyrazolo[3,4-d]pyrimidine, and wherein the different sequences include the wild-type target sequence and different mutant target sequences, (c) incubating the polynucleotide with the array under hybridization conditions, and (d) determining which of the oligonucleotides in the array become hybridized to the polynucleotide;
wherein hybridization of the polynucleotide to oligonucleotides including the wild-type sequence indicates the lack of a mutation, and hybridization of the polynucleotide to oligonucleotides including a mutant sequence indicates the presence of a mutation whose sequence is defined by the particular oligonucleotide to which the polynucleotide is hybridized.

9. A method for identifying a variant of a target sequence, the method comprising the following steps:

(a) providing a sample comprising one or more polynucleotides to be tested for the presence of the variant sequence;

(b) providing at least two oligonucleotides of known sequence wherein one or more purine residues of the oligonucleotides are substituted by a pyrazolo[3,4-d] pyrimidine, and wherein one of the at least two oligonucleotides has a sequence that is perfectly complementary to the target sequence and one or more of the other oligonucleotides has a sequence that is perfectly complementary to one or more variant sequences;

(c) separately incubating each of the oligonucleotides with the polynucleotide under hybridization conditions; and (d) determining the degree of hybridization between each of the oligonucleotides and the polynucleotide;
wherein hybridization of the polynucleotide to the oligonucleotide having a sequence that is perfectly complementary to the target sequence indicates the absence of a variant, and hybridization of the poly nucleotide to an oligonucleotide having a sequence that is perfectly complementary to a particular variant sequence indicates the presence of a variant whose sequence is defined by the oligonucleotide to which the polynucleotide is hybridized.

10. The method of claim 9 wherein the variant sequence is a mutant.

11. The method of claim 9 wherein the variant sequence is a single nucleotide polymorphism.

12. The method of claim 9 wherein the oligonucleotides constitute part of an oligonucleotide array.

13. The method according to claim 2, wherein the minor groove binding moiety is selected from the group consisting of the trimer of 3-carbamoyl-1,2-dihydro-(3H)-pyrrolo[3,2-e]indole-7-carboxylate ($CDPI_3$) and the pentamer of N-methylpyrrole-4-carbox-2-amide ($MPC_5$).

* * * * *

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 510 base pairs
      (B) TYPE: nucleic acid
      (C) STRANDEDNESS: single
      (D) TOPOLOGY: linear (xi) SEQUENCE DESCRIPTION: SEQ ID NO:1:

AAAACTCTCA AGGATCTTAC CGCTGTTGAG ATCCAGTTCG ATGTAACCCA CTCGTGCACC   60

```
CAACTGATCT TCAGCATCTT TTACTTTCAC CAGCGTTTCT GGGTGAGCAA AAACAGGAAG      120

GCAAAATGCC GCAAAAAAGG GAATAAGGGC GACACGGAAA TGTTGAATAC TCATACTCTT      180

CCTTTTTCAA TATTATTGAA GCATTTATCA GGGAATTCGA GAGCCCTGCT CGAGCTGTGG      240

TGGGGTTCCC GAGCGGCCAA AGGGAGCAGA CTCTAAATCT GCCGTCATCG ACTTCGAAGG      300

TTCGAATCCT TCCCCCACCA CCACGGCCGA AATTCGGTAC CCGGATCCTT AGCGAAAGCT      360

AAGATTTTTT TTACGCGTGA GCTCGACTGA CTCCNNNNNN NNGAGCTCAA TTCGGTCGAG      420

GTCGGGCCGC GTTGCTGGCG TTTTTCCATA GGCTCCGCCC CCCTGACGAG CATCACAAAA      480

ATCGACGCTC AAGTCAGAGG TGGCGAAACC                                      510
```

(2) INFORMATION FOR SEQ ID NO:2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:2:

```
CTGGGTGAGC AAAAACAGGA AGGC                                             24
```

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:3:

```
TGTGATGCTC GTCAGGGGGG                                                  20
```

(2) INFORMATION FOR SEQ ID NO:4:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:4:

```
TTCCCGAGCG GC                                                          12
```

(2) INFORMATION FOR SEQ ID NO:5:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:5:

```
GGGTTCCCGA GCGGC                                                       15
```

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:6:

GTGGGGTTCC CGAGCGGC                                              18

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:7:

GTGGGGTTCC CGAGCGGC                                              18

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:8:

GTGGAGTTCC CGAGCGGC                                              18

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:9:

GTGGGGTTTC CGAGCGGC                                              18

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:10:

GTGGGGTTGC CGAGCGGC                                              18

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:11:

GTGGGGTTAC CGAGCGGC                                              18

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:12:

```
GTGGGGTTCT CGAGCGGC                                                          18
```

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:13:

```
GTGGGGTTCA CGAGCGGC                                                          18
```

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:14:

```
GTGGGGTTCC CCAGCGGC                                                          18
```

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:15:

```
GTGGGGTTCC CGTGCGGC                                                          18
```

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:16:

```
GTGGGGTTCC CGAACGGC                                                          18
```

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:17:

```
GTGGGGTTCC CGACCGGC                                                          18
```

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:18:

```
GTGGGGTTCC CGAGCAGC                                                          18
```

(2) INFORMATION FOR SEQ ID NO:19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:19:

GTGGGGTTCC CGAGCTGC                                          18

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:20:

GTGGGGTTCC CGAGCGTC                                          18